US007185653B2

(12) United States Patent
Lee

(10) Patent No.: US 7,185,653 B2
(45) Date of Patent: Mar. 6, 2007

(54) DISPOSABLE MASK FOR DUST PROTECTION

(75) Inventor: Sang-Ho Lee, Anseong-Si (KR)

(73) Assignee: INSAN Co., Ltd., Yongin-Si (KR)

(*) Notice: Subject to any disclaimer, the term of this patent is extended or adjusted under 35 U.S.C. 154(b) by 0 days.

(21) Appl. No.: 10/937,370

(22) Filed: Sep. 10, 2004

(65) Prior Publication Data

US 2005/0051172 A1 Mar. 10, 2005

(30) Foreign Application Priority Data

| | | |
|---|---|---|
| Sep. 9, 2003 | (KR) | 20-2003-0029001 |
| Sep. 9, 2003 | (KR) | 20-2003-0029002 |
| Feb. 2, 2004 | (KR) | 20-2004-0002408 |

(51) Int. Cl.
*A62B 7/10* (2006.01)
*A62B 18/08* (2006.01)
*A61M 16/00* (2006.01)

(52) U.S. Cl. ........................... 128/206.19; 128/206.12; 128/206.13; 128/207.11; 128/207.17

(58) Field of Classification Search ........... 128/206.19, 128/206.12, 206.13, 206.27, 207.11, 207.17, 128/204.11, 206.15, 205.25
See application file for complete search history.

(56) References Cited

U.S. PATENT DOCUMENTS

| | | | | |
|---|---|---|---|---|
| 3,971,369 | A * | 7/1976 | Aspelin et al. | 128/206.19 |
| 4,248,220 | A * | 2/1981 | White | 128/206.19 |
| 4,688,566 | A * | 8/1987 | Boyce | 128/206.19 |
| 5,181,280 | A * | 1/1993 | Zachry, Jr. | 2/452 |
| 5,205,021 | A * | 4/1993 | Durand | 24/163 R |
| 5,699,792 | A * | 12/1997 | Reese et al. | 128/206.19 |
| 6,394,090 | B1 * | 5/2002 | Chen et al. | 128/206.12 |
| 6,427,693 | B1 * | 8/2002 | Blackstock et al. | 128/205.27 |
| 6,484,722 | B2 * | 11/2002 | Bostock et al. | 128/206.19 |
| 2003/0154984 | A1 * | 8/2003 | Fernandes | 128/205.27 |

* cited by examiner

*Primary Examiner*—Henry Bennett
*Assistant Examiner*—Andrew Bunin
(74) *Attorney, Agent, or Firm*—GWiPS

(57) ABSTRACT

A disposable mask for dust protection is provided for maintaining contact with the wearer's face even when moving one's mouth, in which the strap is fixed to maintain tension, and to enable easy adjustment of the length of the strap. The disposable dust protective mask includes a filter body having a front filter, upper and lower sealing wings coupled to the front filter such that they can fold which closely contact the ridge of the nose and the jaw of the wearer, first spread-guiding lines, formed at respective sides corresponding to the front filter, for guiding the upper and lower sealing wings to be spread, second spread-guiding lines for guiding the upper and lower sealing wings to be spread, strap adjusting devices coupled to both sides of the filter body, and a strap connected to the strap adjusting devices and hung on the wearer. The upper and lower sealing wings spread apart along the first and second spread-guiding lines depending on movement of the wearer's mouth and jaw.

9 Claims, 12 Drawing Sheets

DISPOSABLE MASK FOR DUST PROTECTION

BACKGROUND OF THE INVENTION

1. Field of the Invention

The present invention relates to a disposable mask for dust protection. More particularly, the disposable mask for dust protection guarantees freedom of movement while maintaining adhesive force even when the wearer speaks or moves their jaw, maintains tension on the strap, and enables easy adjustment of the length of the strap.

2. Related Prior Art

Generally, a lot of dust is generated in areas such as paper mills, textile factories, quarries, and the like, and large quantities of poisonous gases are generated in areas such as various chemical processing plants, welding processing factories, metal processing factories, plating factories, and the like. Since, in the event that a worker continuously inhales dust and poisonous gases, the dust and poisonous gases can cause respiratory diseases in organs, such as the lungs, throat, nose, and the like, which may be fatal, workers wear a dust protective mask in order to protect themselves from these harmful substances.

There are various types of dust protective masks, e.g., a dust protective mask containing a purifying agent, or a dust protective mask with filter paper installed therein. However, these dust protective masks are expensive, and furthermore, the purifying agent must be exchanged every 3 or 4 days. Moreover, since the above-mentioned dust protective masks do not sufficiently filter the dust or poisonous gases, disposable dust protective masks are usually used when the workers' health must be guaranteed.

The conventional dust protective mask (hereinafter referred to as a "mask") includes a filter made of non-woven fabric and straps connected to the filter.

Since the mask must be discarded after wearing once, it has a limited ability to filter dust present in the air, and the like.

Other masks have been proposed to overcome the above-mentioned shortcoming. For example, the conventional mask includes a folded filter and straps connected to both sides of the filter by means of high frequency sewing. The folded filter is made by bending a front side of the mask several times and by finishing both ends thereof.

According to the above-mentioned mask, the filter is uniformly attached to the nose and lower side of the jaw of the user while the filter is unfolded, so that the efficiency of dust filtering may be increased. However, when the filter is unfolded upward and downward, central portions of the sides of the filter are bent, so that a gap is formed between the user's face and the mask. Thus, the filtering capacity is deteriorated.

There is another mask proposed to overcome the drawbacks. The mask includes a filter having folding portions provided at the upper and lower sides of the filter and finishing portions at both sides of the filter, adjustable straps installed in the respective finishing portions, and a pressing device coupled to the folding portions.

According to the above-mentioned mask, the upper and lower folding portions are unfolded when wearing the mask, and, at the same time, the upper and lower folding portions are closely attached to the user's nose and the lower side of the jaw. The finishing portions of the filter are not folded, and the filter is closely attached to the user's cheeks. Thus, the filtering efficiency can be increased. However, since the upper and lower folding portions of the filter have sufficient restoring elasticity, the unfolded shape when wearing the mask is unstable. Moreover, if the user moves their mouth and/or jaw when wearing the mask, the initial fit of the mask is changed so that the gap between the mask and the user's face is gradually increased.

Further, since the conventional mask employs a metal plate pressing device or a wire-shaped pressing device attached to the folding portions, the pressing device is not closely attached to the user's face, allowing it to easily become unfastened.

There are shortcomings in other conventional masks as well. Since the conventional mask is manufactured assuming that the user keeps their mouth closed and does not move their jaw when wearing the mask, the conventional mask may be stably attached to the user's face when the user has their mouth closed and does not move their jaw. However, if the user moves their jaw in order to have a conversation or to move their lips when wearing the mask, since there is no space in the conventional mask, the conventional mask must be moved up, down, right, or left. For this reason, there is formed a gap where dust flows in between the user's face and the mask. Therefore, it is inconvenient to adjust the position of the conventional mask in order to prevent dust from entering.

Meanwhile, according to the conventional mask, the length of the straps can be adjusted in accordance with the contours and size of the user's face, but there is no special means for adjusting the length of the straps. Since the length of the straps is adjusted by tying the straps, it is inconvenient to repeat the tying and untying of the straps depending on the contours of the user's head when wearing and taking off the conventional mask, or adjusting the length of the straps.

SUMMARY OF THE INVENTION

Therefore, the present invention has been made in view of the above problems, and it is an object of the present invention to provide a disposable dust protective mask for guaranteeing freedom of movement while maintaining adhesive force even when the wearer speaks or moves their jaw, for increasing the tension on the straps, and for preventing the position of the disposable dust protective mask from being changed even when the user has a conversation or moves their lips.

It is another object of the present invention to provide a disposable dust protective mask for maintaining the length of straps in the adjusted state when a user wears the disposable dust protective mask and for providing convenient adjustment of the length of the straps.

In accordance with an aspect of the present invention, the above and other objects can be accomplished by the provision of a disposable dust protective mask including a front filter, upper and lower sealing wings whose ends are coupled to upper and lower portions of one side of the front filter such that they can fold, first and second spread-guiding lines formed on the upper and lower sealing wings in turn at a predetermined distance departing from the ends of the upper and lower sealing wings which are coupled to the front filter, so that the mask is usually spread along the second set of spread-guiding lines, but is spread along the first set of spread-guiding lines when the wearer's mouth or jaw moves—thus the upper and lower sealing wings always adhere to the wearer's face.

Preferably, the disposable dust protective mask according to the present invention further includes a strap adjusting device for elastically fixing the strap and maintaining the tension of the strap so as to easily adjust the length of the strap.

BRIEF DESCRIPTION OF THE DRAWINGS

These and/or other objects and advantages of the present invention will become apparent and more readily appreciated from the following description of the embodiments, taken in conjunction with the accompanying drawings, in which:

FIGS. 6*a* to 6*f* are views illustrating how to wear the disposable dust protective mask according to the present invention, in which:

FIG. 6*a* is a view illustrating a user hanging the disposable dust protective mask according to the present invention around their neck.

FIG. 6*b* is a view illustrating the user wearing the disposable dust protective mask according to the present invention on their face.

FIG. 6*c* is a view illustrating the user pulling a strap of the disposable dust protective mask according to the present invention.

FIG. 6*d* is a front view illustrating the user wearing the disposable dust protective mask according to the present invention.

FIG. 6*e* is a side view illustrating the user wearing the disposable dust protective mask according to the present invention.

FIG. 6*f* is a side view illustrating that the attaching wings of the disposable dust protective mask according to the present invention have been extended in order that the user may have a conversation when wearing the disposable dust protective mask according to the present invention.

DETAILED DESCRIPTION OF THE PREFERRED EMBODIMENTS

Figure 1:
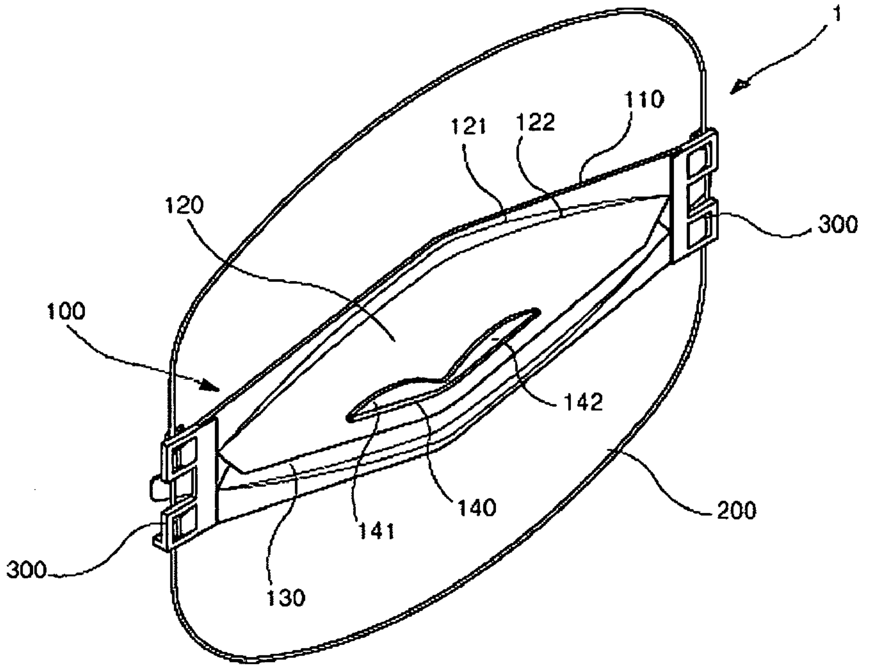
FIG. 1 is a perspective view illustrating a folded state of a disposable dust protective mask according to the present invention.
Figure 2:
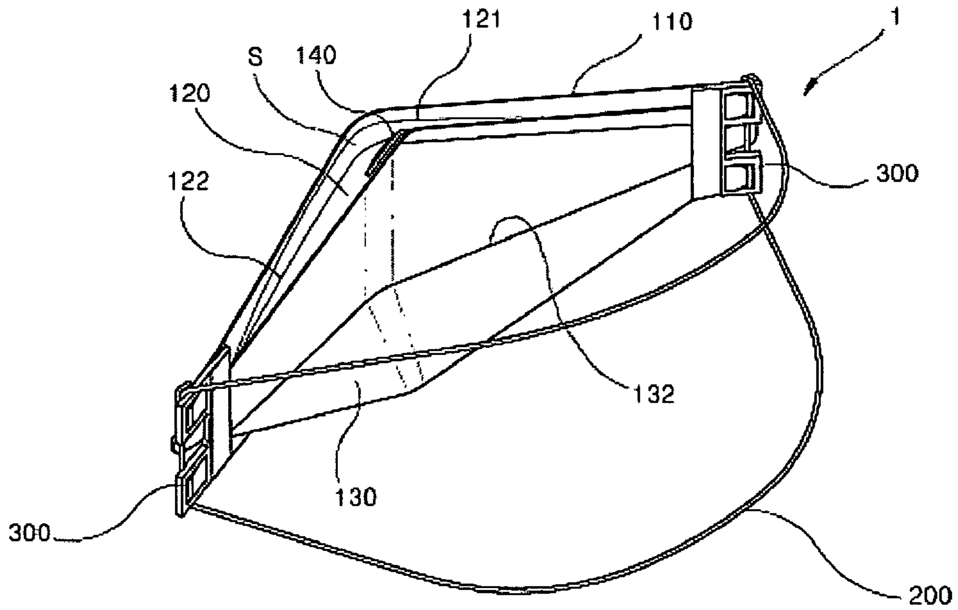
FIG. 2 is a perspective view illustrating the disposable dust protective mask according to the present invention unfolded along a second spread guiding line.
Figure 3:
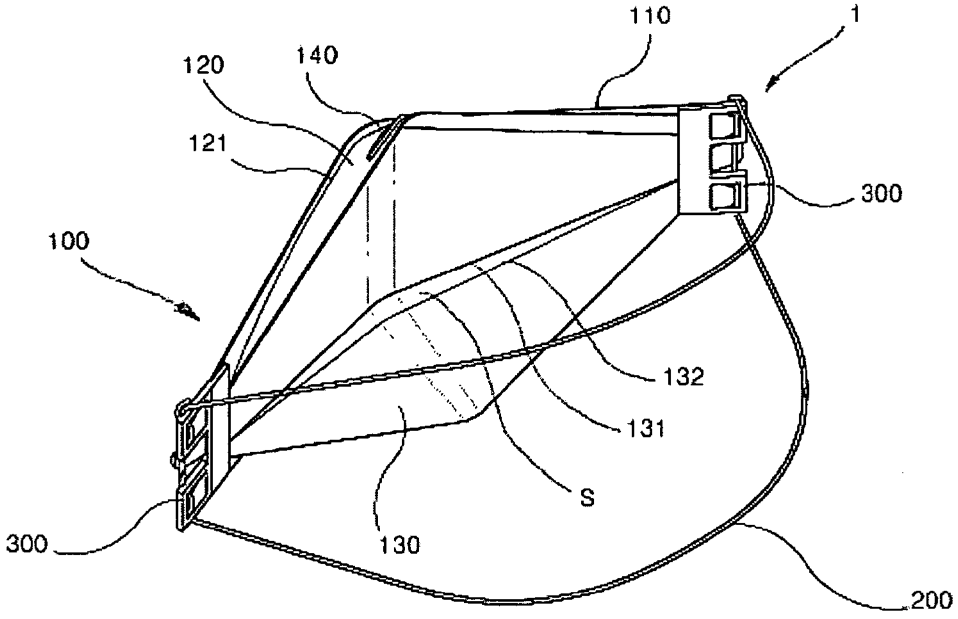
FIG. 3 is a perspective view illustrating the disposable dust protective mask according to the present invention unfolded along a first spread guiding line.

As shown in FIGS. 1 to 3, a disposable dust protective mask according to the present invention includes a filter body 100, strap adjusting devices 300 coupled to respective sides of the filter body 100, and a strap 200 connected to the respective sides of the filter body 100 and hung on some part of the user's body, such as the head, neck, ears, et cetera.

The filter body 100 has a front filter 110 and sealing wings 120 and 130. The sides of the sealing wings 120 and 130 are connected to the upper and lower portions of the front filter 110, respectively, sealing wings on the side of the filter that faces the wearer, such that the wings 120 and 130 can be folded. The sealing wings 120 and 130 closely adhere to the ridge of the wearer's nose and jaw, respectively. The upper and lower sealing wings 120 and 130, as shown in FIG. 1, are maintained to partially overlap each other on one side of the front filter 110, and are unfolded upward and downward on the front filter 110, respectively, as shown in FIG. 2, when wearing the disposable dust protective mask of the present invention.

The front filter 110 is formed in a lozenge shape (a central portion thereof protrudes upward and downward more than other portions), which most accurately conforms to the contours of the wearer's face.

The upper and lower sealing wings 120 and 130 are coupled to the front filter on the upper side or lower side thereof by sewing or the like, and are formed in the width direction. Thus, the wings 120 and 130 have first and second arc-shaped spread-guiding lines 121 and 131, and 122 and 132 for guiding the upper and lower sealing wings 120 and 130.

The first arc-shaped spread-guiding lines 121 and 131 may start from a central region of the front filter 110 and run toward both side central portions of the front filter 110 along inclined sewing lines. The second arc-shaped spread-guiding lines 122 and 132 are joined at the ends of the first arc-shaped spread-guiding lines 121 and 131, and their central portions are formed by arc-shaped folding lines departing from the central portions by a predetermined distance. The second arc-shaped spread-guiding lines 122 and 132 may be formed permanently on the sealing wings 120 and 130 or only when wearing the mask 1.

Here, since the first arc-shaped spread-guiding lines 121 and 131 are formed in an arc shape, there is a height difference between the central portions thereof and both sides. Thus, margins corresponding to the height difference are guaranteed, and the sealing wings 120 and 130 are unfolded and spread due to the margins S. In other words, the margins S are formed between the first spread-guiding lines 121 and 131 and the second spread-guiding lines 122 and 132.

Figure 4:
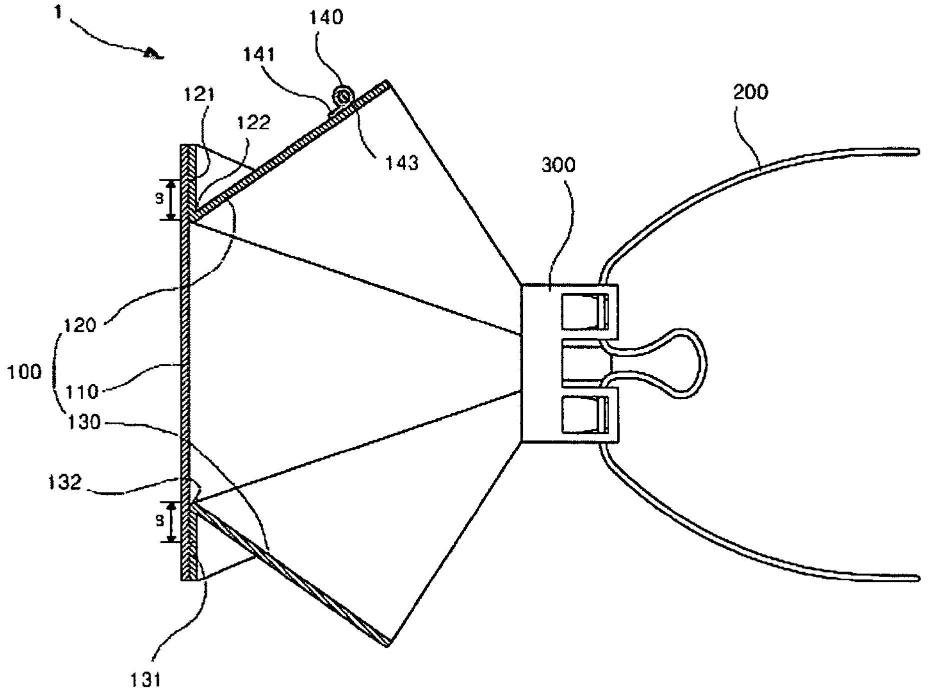
FIG. 4 is a cross sectional side view illustrating the disposable dust protective mask according to the present invention unfolded along the second spread-guiding line.
Figure 5:
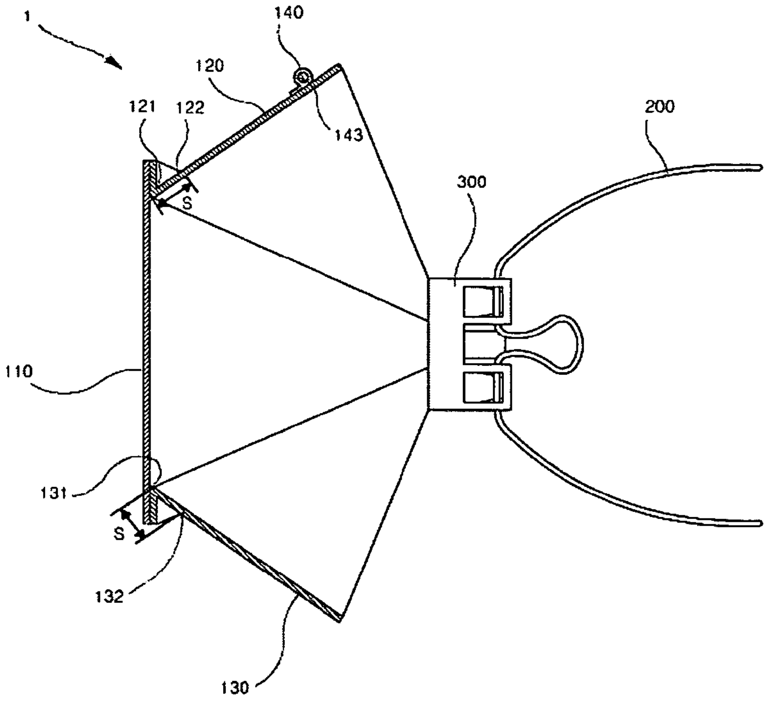
FIG. 5 is a cross sectional side view illustrating the disposable dust protective mask according to the present invention unfolded along the first spread-guiding line.

In the event that the wearer of the mask 1 does not move their lips, as shown in FIGS. 2 and 4, the sealing wings 120 and 130 are unfolded along the second spread-guiding lines 122 and 132 and the margins S are folded. If the wearer opens their mouth and moves their jaw in order to have a conversation, as shown in FIGS. 3 and 5, the margins S are spread apart and the sealing wings 120 and 130, adhering to the wearer's face, are spread apart along the first spread-guiding lines 121 and 131. At the same time, the front filter 110 is pushed forward.

If the distance between the right and left ends of the respective vertically symmetrical spread-guiding lines 121 and 122 and 131 and 132 is changed, the disposable dust protective mask 1 can be optimized for various purposes. For example, if the vertical distance between the right and left ends of the spread-guiding lines 121 and 122 of the upper adhesive wing 120 and the spread-guiding lines 131 and 132 of the lower adhesive wing 130 is narrowed, the sealing wings 120 and 130 are pulled so that the adhesive force of the mask 1 against the wearer's face is increased. Therefore, the disposable dust protective mask 1 can be used in various industries demanding high efficiency dust protection. On the other hand, if the vertical distance is increased, the force applied to the wearer's face is decreased so that the disposable dust protective mask 1 can be used as a common sanitary mask.

Moreover, in order to closely adhere the upper adhesive wing 120 to the ridge of the wearer's nose, the upper adhesive wing 120 is additionally coupled with a pressing device 140 at the outer central portion of the upper adhesive wing 120.

The long pressing device 140 is provided with streamlined pressing wings 141 and 142 on the right and left sides thereof. A pressing wire 143 is inserted into the inside of the pressing device 140. Due to the pressing wire 143 of the pressing device 140 with the above-described structure, the upper adhesive wing 120 adheres to the wearer's face at the most ideal angle with respect to the wearer's face, and the disposable dust protective mask 1 has a more stable and stronger contact force against the wearer's face.

Moreover, the front filter 110 is equipped with an exhaust device 150 that is opened and closed by a suction plate 151 at an outer side thereof, so that the wearer may breathe more easily.

The strap 200 is formed by one closed curved line, and connected to the right and left sides of the filter body 100, so that the strap 200 is hung around the wearer's neck and head. Alternatively, a pair of straps may be provided and respectively connected to the right and left sides of the filter body 100 so as to be hung on the wearer's ears. Regardless of the strap's shape, the strap length can be adjusted by the strap adjusting devices 300.

The operation of the disposable dust protective mask 1 with the above-described structure of the present invention will now be described.

As shown in FIG. 1, the disposable dust protective mask 1 according to the present invention maintains the upper and lower sealing wings 120 and 130 such that they overlap each other and are folded onto one side of the front filter 110.

In order to wear the disposable dust protective mask 1, as shown in FIG. 2, if both sides of the front filter 110 are gathered along the contours of the wearer's face, the upper and lower sealing wings 120 and 130 are spread upward and downward, respectively, while the central portion of the front filter 110 is folded into a streamline shape due to the lozenge shape of the front filter 110. Simultaneously with the spreading of the front filter 110 and the sealing wings 120 and 130, a space where the wearer's nose, mouth, and jaw can be accommodated is guaranteed on the inside of the disposable dust protective mask 1.

Figure 6A:
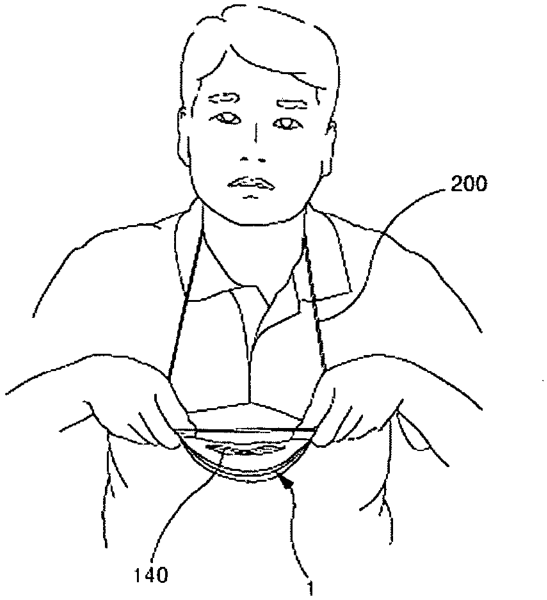
Figure 6B:
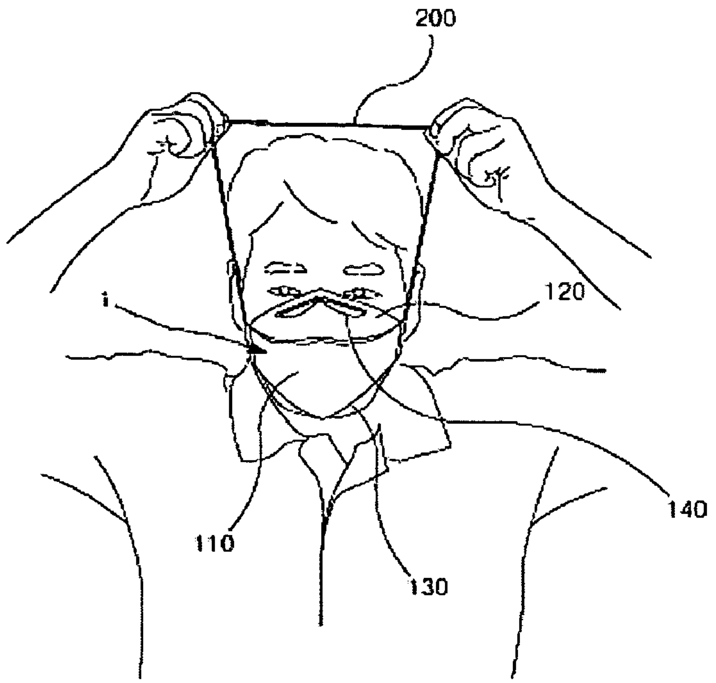
Figure 6C:
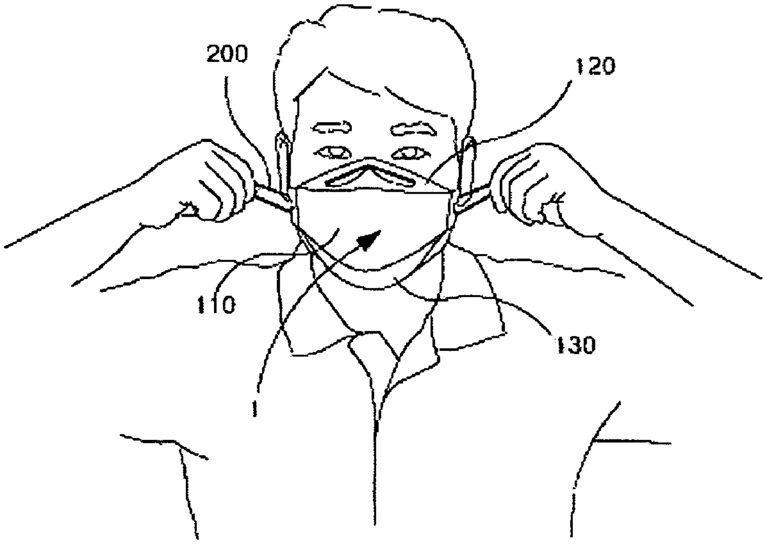
Figure 6D:
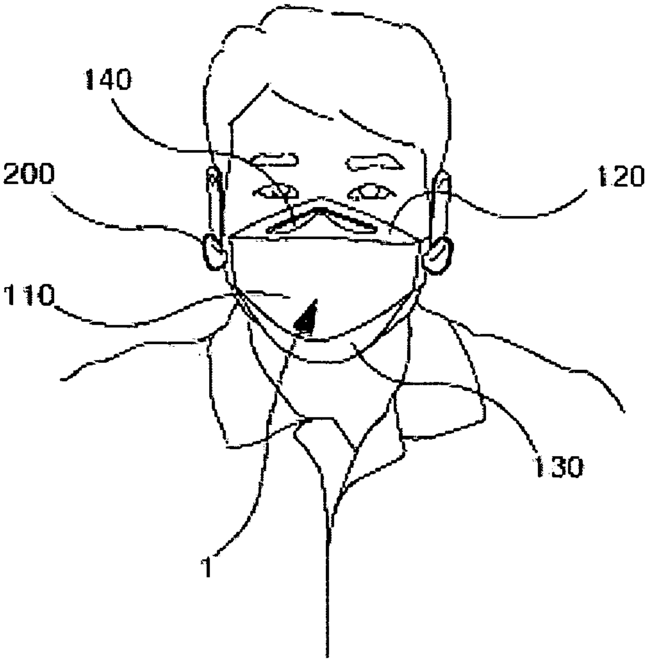
Figure 6E:
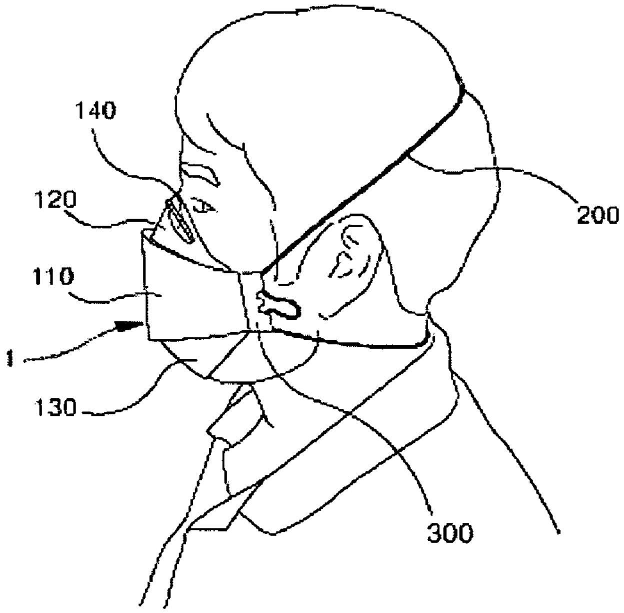
Figure 6F:
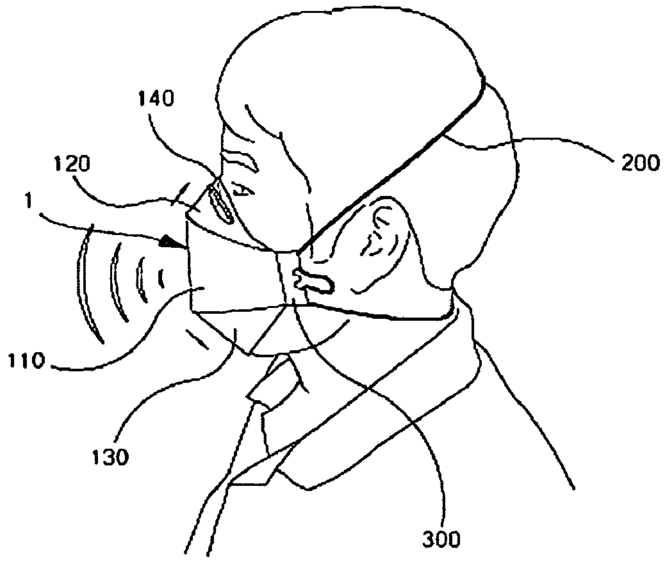

In the same motion, the wearer hangs one side (the lower side in the view of the drawing) of the strap 200 around the wearer's neck as shown in FIG. 6*a*, and hangs the upper portion (as viewed in the drawing) of the strap 200 around the head with the mask 1 positioned on the wearer's face as shown in FIG. 6*b*. Next, as shown in FIG. 6*c*, the wearer pulls both sides of the strap 200 so as to adhere the mask 1 to the wearer's face, and then the process of putting on the mask 1 is finished as shown in FIG. 6*d* (the length adjustment of the strap 200 will be described in detail when the strap adjusting device is described below).

When wearing the disposable dust protective mask 1, since the sides of the sealing wings 120 and 130 are maintained along the face contours and vertically spread, the sealing wings 120 and 130 maintain contact with the wearer's profile so that firm adhesion can be achieved without gaps.

Hereinafter, the operations of the first and second spread-guiding lines 121, 131, 122, and 132 will be described.

If the wearer does not open their mouth when wearing the mask 1, since the sealing wings 120 and 130 are pulled to the right and left by forces applied to the sides of the sealing wings 120 and 130, as shown in FIGS. 2 and 4, the sealing wings 120 and 130 are spread, keeping the margins S folded together about the right and left sides of the first spread-guiding lines 121 and 131, and therefore the second spread-guiding lines 122 and 132 are formed.

While wearing the mask in this fashion, if the wearer opens their mouth due to movement, such as conversation, yawning, or the like, forces caused by the wearer's action, as shown in FIGS. 3 and 5, cause the sealing wings 120 and 130 to expand and spread upward and downward to the first spread-guiding lines 121 and 131 through the margins S. Because of this, the wearer can move the temporomandibular joint without changing the positions of the sealing wings 120 and 130 adhered to the ridge of the wearer's nose and lower jaw.

In this state, if the wearer closes their mouth, the forces exerted on the disposable dust protective mask 1 are removed, thus the sealing wings 120 and 130 are restored to the state as shown in FIGS. 2 and 4 while re-forming the second spread-guiding lines 122 and 132 due to forces applied to the sides of the sealing wings 120 and 130.

In other words, though the wearer continues conversing or opens and closes their mouth as desired while wearing the mask 1, the sealing wings 120 and 130 are smoothly folded along the first and second spread-guiding lines 121, 131, 122, and 132, so that the mask 1 remains in contact with the wearer's face.

Moreover, if the wearer bends the pressing device 140 that is coupled to the upper adhesive wing 120 as shown in FIG. 6*d* inward toward the wearer's face, the pressing wire 143 in the pressing device 140 adheres to the ridge of the wearer's nose and both lower pressing wings 141 and 142 press the adhesive wing 120 toward the wearer's face. Thus, the upper adhesive wing 120 firmly adheres to the wearer's face.

Figure 7:
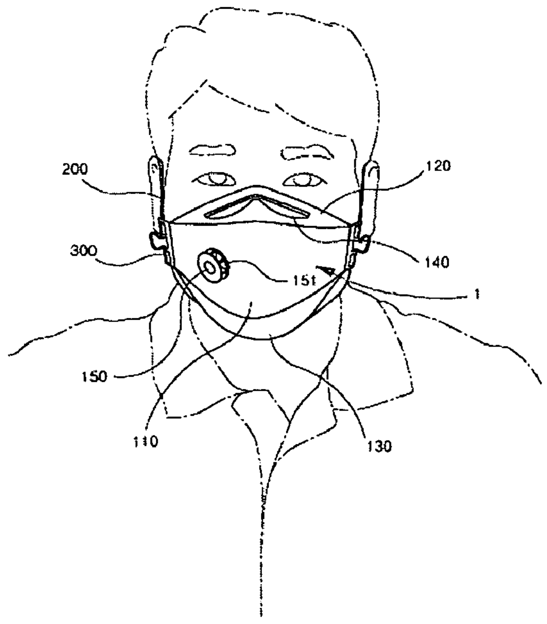
FIG. 7 is a view illustrating that the disposable dust protective mask according to the present invention employs an exhaust device.

The disposable dust protective mask 1 according to the present invention, as shown in FIG. 7, is provided with a well-known exhaust device 150 that is opened and closed by a suction plate 151 on one side of the front filter 110 so that the wearer may breathe more easily through the exhaust device 150.

In detail, when inhaling, since the suction plate 151 adheres to the exhaust device 150 so as to close the exhaust device 150, dust and harmful matter is filtered while passing through the front filter 110 and the sealing wings 120 and 130 and the filtered air is introduced to the mask 1. When exhaling, since the suction plate 141 of the exhaust device 150 is pushed out so as to open the exhaust device 150, the wearer can breathe easily.

Hereinafter, the strap adjusting devices 300 employed in the disposable dust protective mask 1 according to the present invention will be described in detail.

Figure 8A:
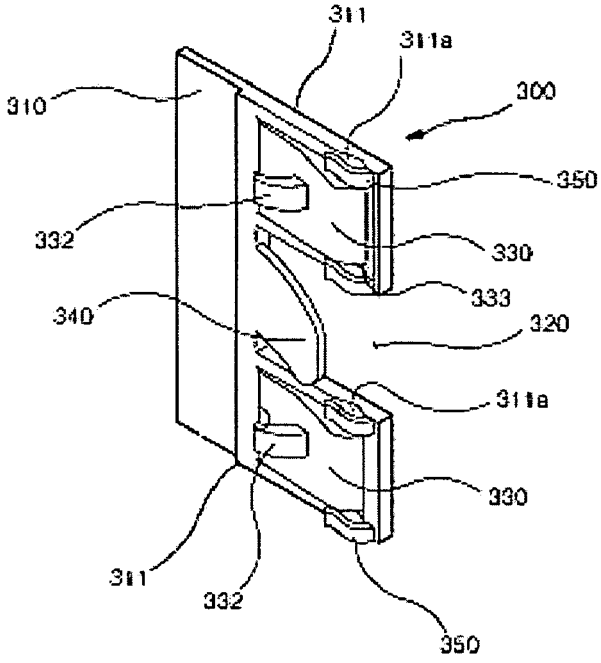
FIGS. 8*a* and 8*b* are a perspective front side view and a perspective rear side view illustrating a strap adjusting device employed in the disposable dust protective mask according to first embodiment of the present invention.
Figure 8B:
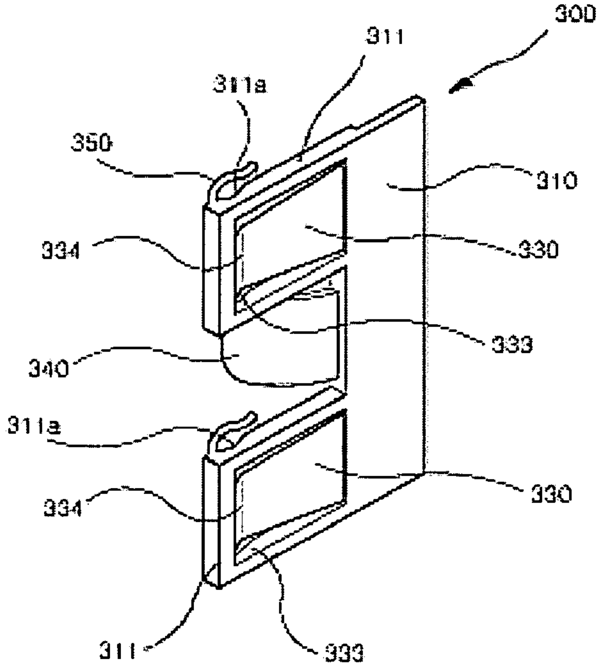

As shown in FIGS. 8*a* and 8*b*, the strap adjusting device 300 employed in the disposable dust protective mask according to the first embodiment of the present invention includes a plate-shaped adjusting body 310, at least one elastic piece 330 provided at the adjusting body 310 for elastically fixing the strap 200, and a guide grip 340 obliquely formed outside of the adjusting body 310.

The elastic pieces 330 may be formed on the upper and lower outer sides of the adjusting body 310, spaced by a predetermined interval in a vertically longitudinal direction, and the number thereof is not limited to two.

Figure 9:
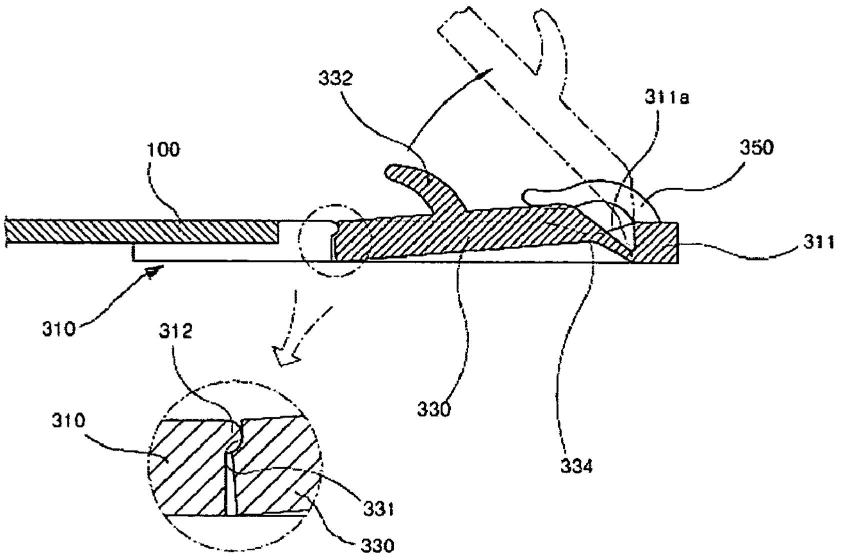
FIG. 9 is a view illustrating the operation of the strap adjusting device employed in the disposable dust protective mask according to the first embodiment of the present invention.

Only one side (the side corresponding to the outside of the frame 311) of each elastic piece 330 is connected inside the approximately quadrangular frame 311. The frame 311 is approximately quadrangular and protrudes from one side of the adjusting body 310. A free end of the elastic piece 330 elastically moves about the connecting portion thereof connected to the frame 311. The free end (the side opposite to the side of the adjusting body 310 connected to the adjusting body 310) of the adjusting body 310 is detachably fixed to the adjusting body 316. The fixing structure of the elastic piece 330, as shown in FIG. 9, for example, is constructed such that the free ends of the elastic pieces 330 are formed with a fixing recess 331 and the adjusting body 310 is formed with a fixing protrusion 312 to be inserted into the fixing recess 331. As such, the elastic pieces 330 can be detachably coupled to the adjusting body 310.

The elastic piece 330 is formed with a protruding grip portion 332 on one side for manipulating the elastic piece 330.

Figure 10A:
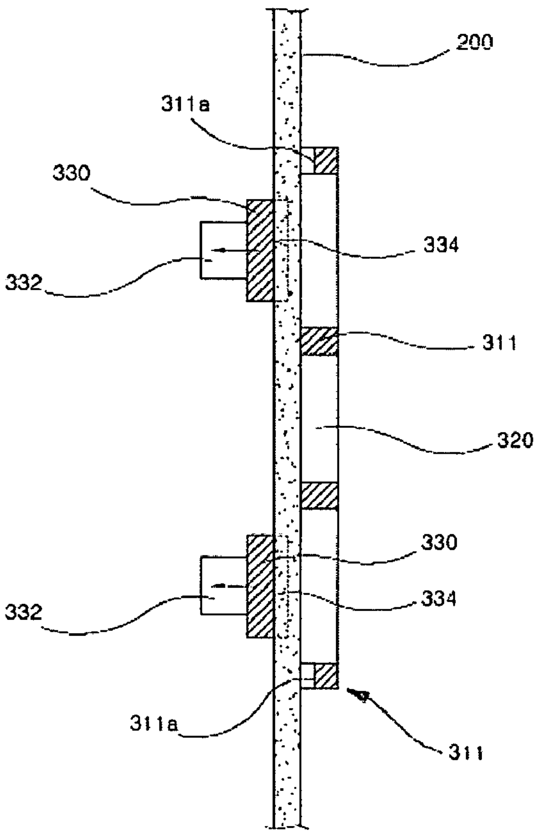
FIGS. 10*a* and 10*b* are cross sectional views illustrating the strap released from and tightly fitted into the strap adjusting device of FIG. 9, respectively.
Figure 10B:
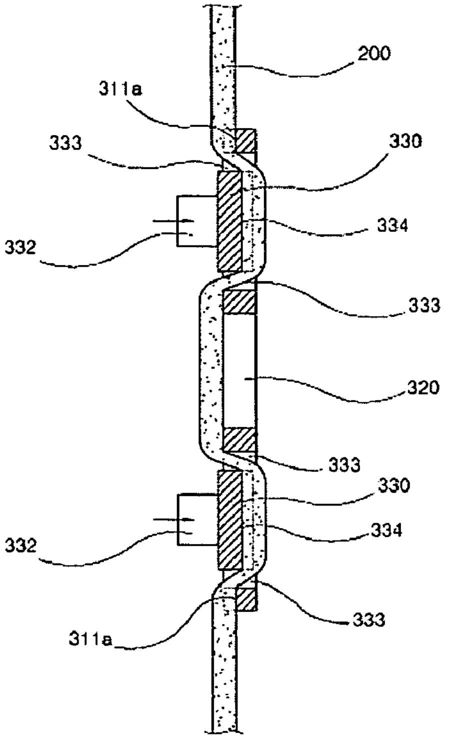

In order to increase the fixing force of the strap 200, as shown in FIG. 10*b*, the upper and lower portions of the elastic piece 330 are formed with spaces in which the strap 200 is inserted, so that the strap 200 is fixed to the elastic piece 330 in a zigzag pattern (the strap 200 contacts the rear side of the elastic piece 330 during contact with the front side of the frame 311).

In order to increase the fixing force of the strap 200 and to fix the strap in the strap adjusting devices 300, the frame 311 of the adjusting body 310 and the rear side of the elastic piece 330 may each be formed with strap inserting recesses 311*a* and 334. In other words, the strap 200 is inserted along the strap inserting recesses 311*a* and 334 and the spaces 333 and is fixed by the elastic piece 330.

Further, when the length of the strap 200 is adjusted, the upper and lower sides of the elastic piece 330 may be further formed with respective separation preventing clips 350 so that the strap 200 does not separate from the strap adjusting devices 300.

The above-described strap adjusting devices 300, as shown in FIG. 9, are coupled to the right and left sides of the filter body 100 of the disposable dust protective mask of the present invention.

The operation of the strap adjusting devices having the above-mentioned structure employed in the disposable dust protective mask according to this embodiment of the present invention will now be described.

The strap adjusting devices 300 serve to fix the strap 200 in place after it is inserted into the strap insertion recesses 311*a* and 334, so that it is not separated therefrom by the elastic pieces 330. The free ends of the elastic pieces 330 are not coupled to the adjusting body 310 when adjusting the length of the strap 200, when taking the mask 1 off, or the like.

In other words, as shown in FIG. 10*a*, since the strap 200 is able to move along the spaces 333 and the strap insertion recesses 311*a* and 334 without friction against the strap adjusting devices 300 or the elastic pieces 330, the length of the strap 200 is adjustable without interference from the elastic pieces 330.

When releasing the strap 200 by separating the elastic pieces 330 from the adjusting body 310 to position the mask 1 on the wearer's face, as shown in FIG. 6*b*, and pulling the strap 200 exposed to spaces 320 in order to adjust the tension on the strap 200, the straps 200 are extracted through the spaces 320 and pass through the spaces 333 and strap insertion recesses 311*a* and 334. By doing so, the strap 200 is tightened on the wearer's head.

When the open elastic pieces are pressed after tightening the strap 200, as shown in FIG. 9, the elastic pieces rotate toward the adjusting body 310 and then the fixing protrusions 312 of the adjusting body 310 are inserted into the fixing recesses 331. Thus, the strap 200 is pressed and fixed by the adjusting devices 300. In more detail, the strap 200 is fixed by the pressure of the elastic pieces 330. As shown in FIG. 10*b*, the strap 200 is bent several times by the frame 311 and the elastic pieces 330 and tightly fixed by the contact force between the frame 311 and the elastic pieces 330.

On the contrary, if taking the disposable dust protective mask 1 off or adjusting the length of the strap 200 while wearing the mask 1 as in the above description, the wearer pulls the protruding grip portion 332. At this time, the elastic pieces 330 are separated from the adjusting body 310 and the strap 200 is released, as shown in FIG. 10. In this state, the wearer adjusts the length of the strap 200 or takes the mask 1 off.

Here, the strap 200 is pressed and fixed by a pair of elastic pieces 330. Since it is possible to release only one elastic piece 330 of the pair of elastic pieces 330 so as to release the strap slightly, the wearer can selectively manipulate a pair of elastic pieces 330 depending on the given circumstances.

Figure 11:
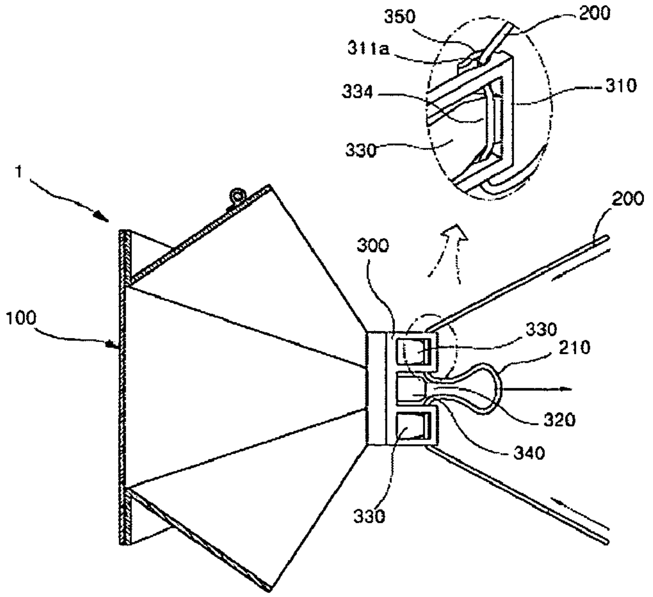
FIG. 11 is a side view illustrating the adjustment of the strap using the strap adjusting device.

Meanwhile, when adjusting the length of the strap 200 by simultaneously pulling both sides of small loops 210, the strap 200 passes through the inner space of the separation preventing clips 350 and does not escape from the strap adjusting devices 300 as shown in FIG. 11.

Hereinafter, another embodiment of the strap adjusting device employed in the disposable dust protective mask of the present invention will be described.

Figure 12:
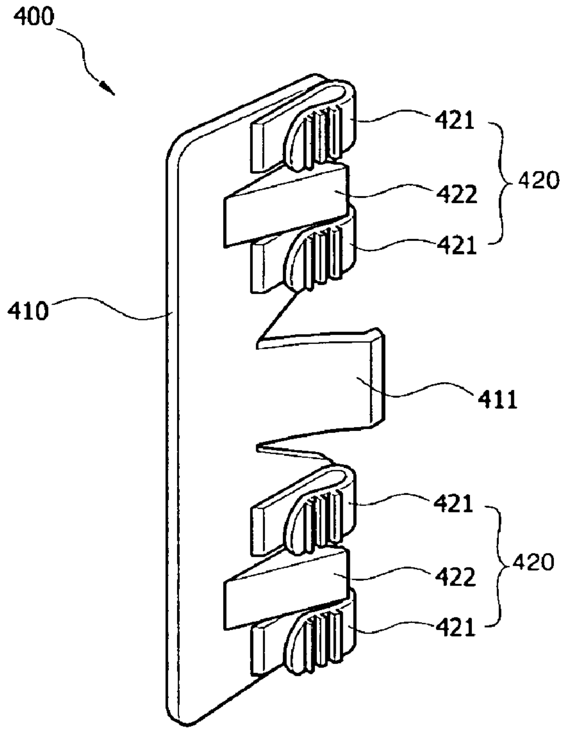
FIG. 12 is a perspective view illustrating a strap adjusting device employed in the disposable dust protective mask according to a second embodiment of the present invention.

As shown in FIG. 12, the strap adjusting device 400 according to this embodiment of the present invention includes an adjusting body 410 and strap fixing sections 420. Two adjusting bodies 410 are coupled to the mask filter body 100 (See FIGS. 14 and 15). A strap 200 (see FIGS. 14 and 15) is connected to each adjusting body 410. The strap fixing sections 420 are formed on the adjusting body 410. The strap fixing sections 420 adjust the length of the strap 200 and maintain the tension of the strap 200 when the strap 200 is connected thereto.

The plate-shaped adjusting body 410 may be fixed to the sides of the mask filter body 100 by sewing, or the like. The length of the adjusting body 410 is slightly less than or equal to the length of the mask filter body 100. The adjusting body 410 has a width sufficient to firmly fix the adjusting body 410 to the mask filter body 100 as well as to allow the strap fixing sections 420 to be formed. Preferably, the adjusting body 410 is as thin as possible.

The strap adjusting sections 420 connect the strap 200 with the adjusting body 410 to adjust the length of the strap 200, and each is provided with at least one first supporting piece 421 and a second supporting piece 422.

Figure 13:
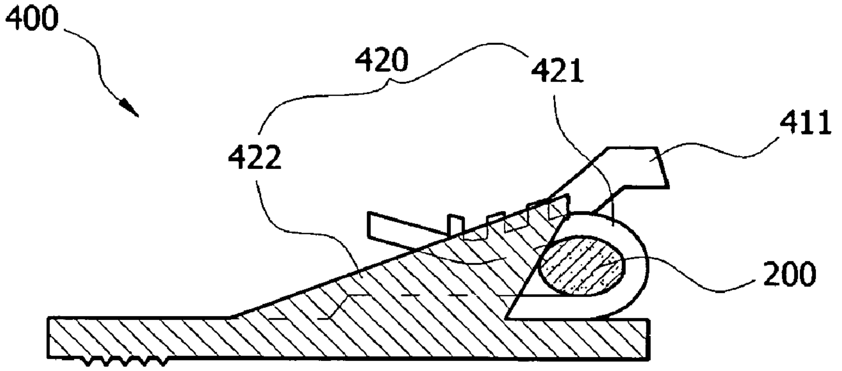
FIG. 13 is a cross sectional view of the strap adjusting device in FIG. 12.

As shown in FIG. 13, the first supporting piece 421 and the second supporting piece 422 support the strap 200 together. For example, the first supporting piece 421 has an open end and is formed with a gap (the gap size is smaller than the thickness of the strap 200 so as to elastically support the strap 200) into which the strap 200 can be inserted, between the adjusting body 410 and the first supporting piece 421. The open end of the first supporting piece 421 is preferably gradually widened in order to easily insert the strap 200 thereinto.

The second supporting piece 422 supports the strap 200 that is inserted into the first supporting piece 421. For example, the second supporting piece 422 is formed with an inclined upper side. The inclined upper side rises from one side portion of the adjusting body 410 toward the outer side of the adjusting body 410 (See FIG. 13). In other words, the first and second supporting pieces 421 and 422 support the strap 200 by supporting the sides of the strap 200.

Preferably, the first and second supporting pieces 421 and 422 are alternately formed along the vertical direction of the adjusting body 410, while the first supporting pieces 421 face each other and have open sides facing the sides of the first and second supporting pieces 421 and 422. For example, since, as shown in FIG. 12, the highest end and the lowest end of the adjusting body 410 are where the strap 200 is inserted, the first supporting piece 421 is arranged at these locations, and the first and second supporting pieces 421 and 422 are alternately arranged between the highest and lowest first supporting pieces 421.

The first and second supporting pieces 421 and 422 may be formed along the vertical direction of the adjusting body 410, and also, if setting plural supporting pieces as one set of supporting pieces, a plurality of sets of supporting pieces may be formed in the local area. The supporting piece can be changed or modified freely.

In this embodiment, a grip helper 411 is further provided in order to easily adjust the length of the strap 200 and to guide a grip of the strap 200. The grip helper 411 is preferably formed with a taper toward the inner side of the adjusting body 410 (as viewed in the drawing), so as to easily grasp the strap 200.

The grip helper 411 may be formed approximately at a central portion of the adjusting body 410, so that the grip helper 411 may be formed between the strap fixing sections 420 formed at the upper and lower sides of the adjusting body 410 comprising the first and second supporting pieces 421 and 422. That is, if employing two first supporting pieces 421 and one second supporting piece 422 therebetween as one set of a strap fixing section 420, the adjusting body 410 has two strap fixing sections 420 (See FIG. 15). Although in the present invention the strap fixing section 420 includes the first supporting piece 421 and the second supporting piece 422, the number and arrangement of the supporting pieces are not limited by the description and the accompanying drawings.

Figure 14:
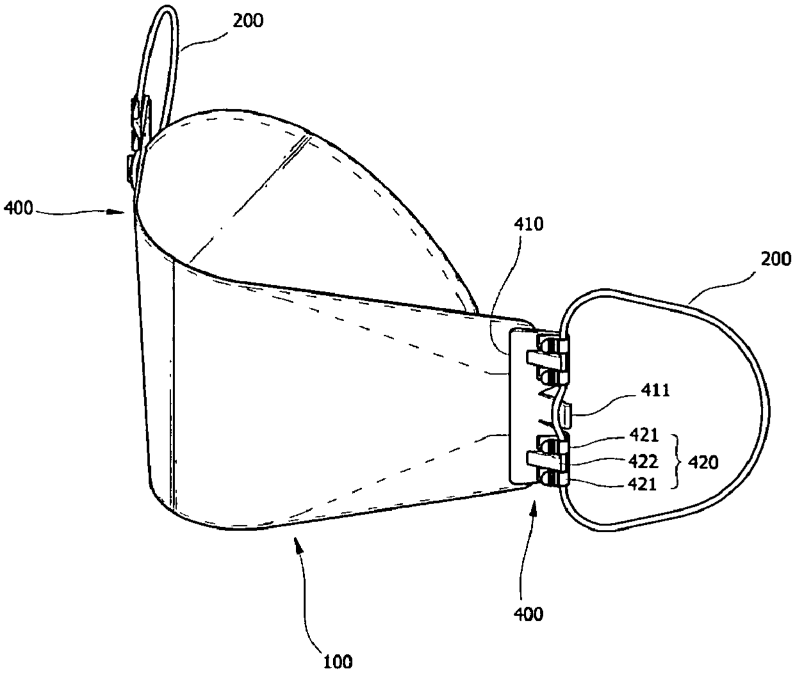
FIG. 14 is a perspective view illustrating the disposable dust protective mask employing the strap adjusting device of FIG. 12.
Figure 15:
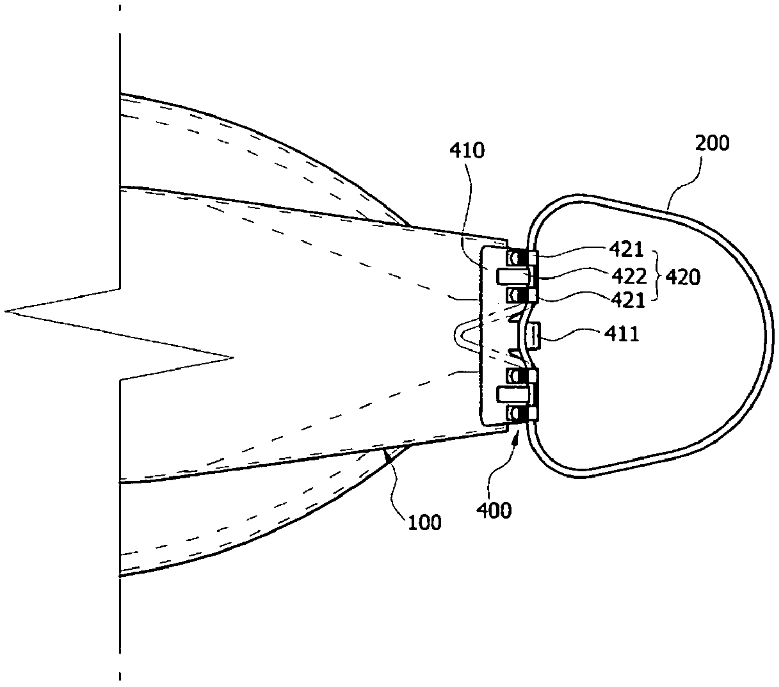
FIG. 15 is a partial cross sectional front view illustrating the disposable dust protective mask employing the strap adjusting device of FIG. 12.
Figure 17:
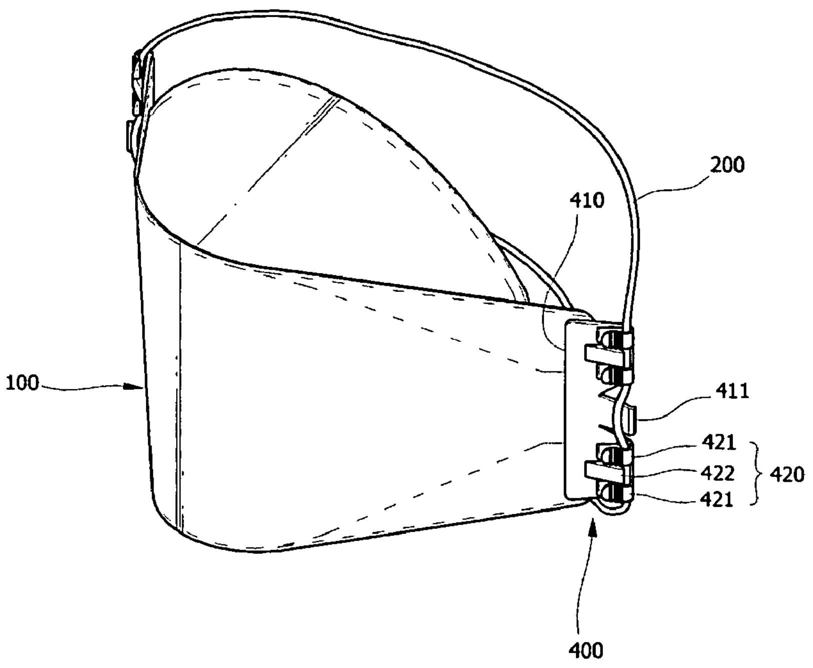
FIG. 17 is a perspective view illustrating the disposable dust protective mask employing the strap adjusting device of FIG. 12 to which another strap is connected.

The strap adjusting devices 400, as shown in FIG. 14, may each be connected to individual straps 200, or, as shown in FIG. 17, a single loop strap 200 may be connected thereto.

The operation of the strap adjusting device according to this embodiment of the present invention will now be described.

As shown in FIGS. 12 and 13, when inserting the strap 200 into the first supporting piece 421 and pulling the inserted strap 200, the strap 200 is naturally inserted into the second supporting piece 422 and placed on the grip helper 411. At this time, the end of the first supporting piece 421 is obliquely bent upward, that is, is gradually spread toward an opening, so that there is no interference when inserting the strap 200 into the first supporting piece 421. There is no need for an additional structure for fixing the strap 200 if the strap 200 is supported in this way by the first and second supporting pieces 421 and 422.

As shown in FIG. 13, since the strap 200 is inserted between the first and second supporting pieces 421 and 422, the strap 200 will not separate from the adjusting body 410. Moreover, since the gap between the first supporting piece 421 and the adjusting body 410 is less than the thickness of the strap 200, the strap 200 is elastically supported by the elastic force of the first supporting piece 421.

Figure 16:
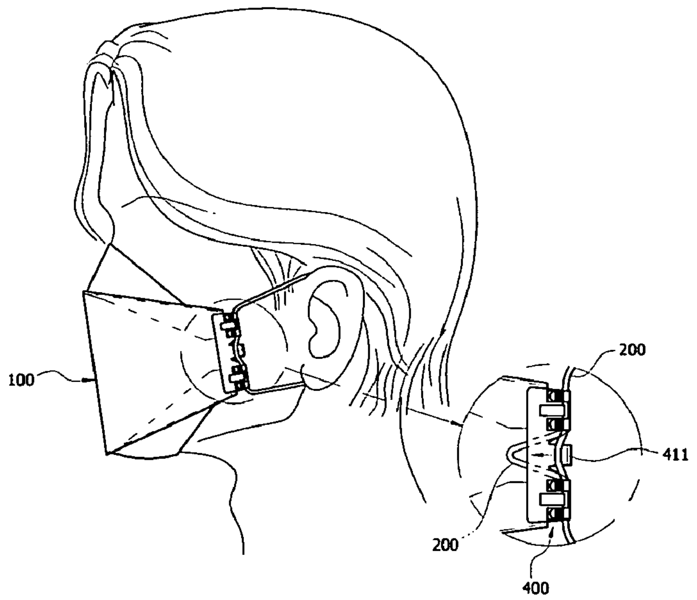
FIG. 16 is a view illustrating the state of wearing the disposable dust protective mask employing the strap adjusting device of FIG. 12.

When the connection of the strap is finished, as shown in FIG. 16, the wearer hangs the strap 200 on their ears, while attaching the mask filter body 100 to their nose and mouth, and uses their fingers (e.g., the thumb and the index finger) to grasp the strap adjusting devices 400 in order to adjust the length of the strap 200. Then, the wearer can naturally grasp the grip helper 411, which is more prominent than the other components of the adjusting body 410. Next, the wearer holds the grip helper 411 together with the strap 200 placed on the grip helper 411 and pulls the strap, so that the strap 200 is pulled and the length of the strap 200 is adjusted.

When the length of the strap 200 is suitable and the wearer removes their fingers from the strap 200, since the strap is maintained at the adjusted state by the pressure between the first and second supporting pieces 421 and 422 against the strap 200 and the elastic force thereof, the disposable dust protective mask 1 is firmly attached to the wearer's face.

As described above, according to the disposable dust protective mask of the present invention, since a space suitable to the wearer's face is formed inside the disposable dust protective mask due to the lozenge-shaped front filter and the spread of the upper and lower sealing wings when wearing the disposable dust protective mask, the adhesive force against the wearer's face is increased. Moreover, even when having a conversation or moving one's lips while wearing the disposable dust protective mask, since the sealing wings are spread starting from the front filter and their adhesive forces are maintained, the reliability of the dust protective mask is enhanced.

Further, since the strap is firmly fixed to the strap adjusting devices by the elastic pieces and its tension is maintained, the mask is comfortable.

In addition, since the connection of the strap is finished by inserting and pulling the strap into the first supporting piece and by then inserting the strap into the second supporting piece, the connection of the strap is easy and productivity is improved.

Finally, since the strap can be grasped by the grip helper without needing to look at the strap when adjusting the length of the strap, adjustment of the length of the strap is convenient.

Although the preferred embodiments of the present invention have been disclosed for illustrative purposes, those skilled in the art will appreciate that various modifications, additions and substitutions are possible, without departing from the scope and spirit of the invention as disclosed in the accompanying claims

What is claimed is:

1. A disposable mask consisting of a filter body and a fastening means for dust protection, the mask comprising:

a front filter (110) formed with a protruded central portion, an upper sealing wing (120) for unfolding to seal wearer's nose, said upper sealing wings (120) having upper first and second spread-guiding lines (121, 122) for inwardly spreading the upper sealing wings, a lower scaling wing (130) for unfolding to seal wearer's jaw, said lower sealing wings (130) having lower first and second spread-guiding lines (131, 132) for inwardly spreading the lower sealing wings, a pressing device (140) disposed at outer central portion of the upper sealing wing (120), a looped strap (200) for wearing around the wearers' head and neck, a pair of strap adjusting devices having a plate-shaped adjusting body for coupling to both sides of the filter body, a pair of upper and lower fastening means including an elastic piece for elastically grasping the looped strap, a pair of inserting recesses at each fastening means, a space between the elastic pieces and the fastening means for inserting the looped strap in a zigzag pattern through the upper and lower fastening means, a guide grip disposed between the upper and lower fastening means and obliquely formed outward for easily pulling both ends of the looped strap at the same time, and a pair of separation preventing clips formed at outer edge of each fastening means for preventing the looped strap off from the path, and a grasping and pulling portion of the looped strap provided at both sides of the guide grips for easily pulling the looped strap, simultaneously fastening and maintaining tension of the looped strap by an elastic holding means.

2. The disposable mask for dust protection as set forth in claim 1, wherein said first and second spread-guiding lines (131, 132) are sewing lines to form an arc shape, which are gradually oblique from a center to both sides of the front filter (110) for unfolding or folding the upper and lower sealing wings (120, 130), said upper spread-guiding line (120) is apart from the lower spread-guiding line (130) by a predetermined width at center of the front filter (110) and decreasing from center to both sides along the arc-shaped folding line.

3. The disposable mask for dust protection as set forth in claim 1, wherein said pressing device (140) further comprises a pair of streamlined pressing wings (141, 142) and an inserted pressing wire (143) for press-bent deforming to seal the wearer's face.

4. The disposable mask for dust protection as set forth in claim 1, further comprises a respiration device (150) attached to the front filter (110).

5. The disposable mask for dust protection as set forth in claim 1, wherein said fastening means comprises a pair of upper and lower frames (311), an elastic piece (330) for elastically grasping the looped strap (200), a pair of inserting recesses (311*a*, 334) at each frame (311), a space (333) between the elastic pieces (330) and the frames (311) for inserting the looped strap (200) in a zigzag pattern through the upper and lower frames, a guide grip (340) disposed between the upper and lower fastening means and obliquely formed outward for easily pulling both ends of the looped strap (200) at the same time, and a pair of separation preventing clips (350) formed on the outer edge of the frames (311) for preventing the looped strap (200) off from the path.

6. The disposable mask for dust protection as set forth in claim 5, wherein a fixing recess (331) formed at a free end of said elastic pieces (330) is detachably coupled to a fixing protrusion (312) formed at a free end of the adjusting body (310) for exerting elastic force.

7. The disposable mask for dust protection as set forth in claim 1, wherein said strap adjusting device (400) comprises an adjusting body (410) for coupling both sides of the filter body (100) and a pair of upper and lower strap fixing devices (420) for grasping the looped strap (200), simultaneously fastening and maintaining tension of the looped strap (200).

8. The disposable mask for dust protection as set forth in claim 7, wherein said strap fixing devices (420) further comprise at least one first supporting piece (421) and a second supporting piece (422) arranged alternatively each other to form a gap with zigzag path for inserting through the first and second supporting pieces of upper and lower strap fixing devices for elastically grasping the looped strap (200).

9. The disposable mask for dust protection as set forth in claim 8, wherein the strap adjusting body (410) further comprises a grip helper (411) for easily pulling both ends of the looped strap (200) at the same time to adjust the tension and fasten the looped strap (200).

* * * * *